(12) United States Patent
Van Halsema

(10) Patent No.: US 9,176,098 B2
(45) Date of Patent: *Nov. 3, 2015

(54) MILK PROPERTY MEASURING DEVICE

(71) Applicant: LELY PATENT N.V., Maassluis (NL)

(72) Inventor: Frans Emo Diderik Van Halsema, Veenendaal (NL)

(73) Assignee: LELY PATENT N.V., Maassluis (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,875

(22) Filed: Jan. 8, 2014

(65) Prior Publication Data
US 2014/0123733 A1 May 8, 2014

Related U.S. Application Data

(63) Continuation of application No. 12/903,230, filed on Oct. 13, 2010, now Pat. No. 8,650,938.

(30) Foreign Application Priority Data

Oct. 13, 2009 (NL) .................................... 1037390

(51) Int. Cl.
*G01N 29/024* (2006.01)
*G01N 33/04* (2006.01)
(Continued)

(52) U.S. Cl.
CPC ............ *G01N 29/024* (2013.01); *A01J 5/0137* (2013.01); *G01K 11/24* (2013.01); *G01N 33/04* (2013.01); *G01K 2207/02* (2013.01); *G01N 2291/02881* (2013.01)

(58) Field of Classification Search
CPC ................ G01N 29/024; G01N 33/04; G01N 2291/02881; G01K 11/24; G01K 2207/02; A01J 5/0137

USPC .................. 73/1.82, 1.83, 1.86, 53.02, 54.25, 73/61.45, 61.46, 61.49, 61.71, 61.75, 73/61.79, 64.53, 597

See application file for complete search history.

(56) References Cited

U.S. PATENT DOCUMENTS

| 3,040,562 A | 6/1962 | Fitzgerald et al. |
| 4,145,450 A | 3/1979 | Winder et al. |

(Continued)

FOREIGN PATENT DOCUMENTS

| EP | 0379280 A2 | 7/1990 |
| EP | 1287737 A2 | 3/2003 |
| SU | 913074 A1 | 3/1982 |

OTHER PUBLICATIONS

Database WPI week 198303, Thomson Scientific, London, GB: AN 1983-A9463K, XP002588721, Mar. 25, 1982.

(Continued)

*Primary Examiner* — Daniel S Larkin
(74) *Attorney, Agent, or Firm* — Hoyng Rokh Monegier LLP; Minerva Rivero; David P. Owen

(57) ABSTRACT

The present invention provides a system and method for a milk measuring device for measuring the acoustic properties, such as acoustic damping and sound velocity in milk, in order to determine milk properties. The sound velocity in milk depends on temperature and composition. By carrying out, for example by means of a piezo element, a reference measurement on vibrations that have been directed by a second piezo element into a wire or the like of known material, which wire is strung in the measuring chamber which is filled with the milk to be tested, the milk temperature can be derived, so that other milk properties, in particular the fat/protein composition, can be determined in a more reliable manner.

20 Claims, 2 Drawing Sheets

(51) Int. Cl.
*G01K 11/24* (2006.01)
*A01J 5/013* (2006.01)

(56) References Cited

U.S. PATENT DOCUMENTS

| | | |
|---|---|---|
| 4,772,131 A | 9/1988 | Varela et al. |
| 5,286,109 A | 2/1994 | Hanscombe et al. |
| 6,044,694 A * | 4/2000 | Anderson et al. ............ 73/54.41 |
| 6,823,716 B2 | 11/2004 | Kelner et al. |
| 7,574,898 B2 * | 8/2009 | Harrison et al. ............. 73/54.41 |
| 2008/0307885 A1 | 12/2008 | Ravitch et al. |

OTHER PUBLICATIONS

Translation Dutch Search Report of NL1037390, Jun. 24, 2010.

\* cited by examiner

MILK PROPERTY MEASURING DEVICE

CROSS REFERENCE TO RELATED APPLICATIONS

This application is a continuation of U.S. patent application Ser. No. 12/903,230, filed on 13 Oct. 2010, now U.S. Pat. No. 8,650,938, which claims priority from Netherlands application number 1037390 filed on 13 Oct. 2009, the contents of which are hereby incorporated by reference in their entirety.

BACKGROUND OF THE INVENTION

Field of the Invention

The invention relates to a milk property measuring device, comprising a measuring chamber which is configured to be filled with milk, a first vibration means provided at a first side of the measuring chamber, configured to generate first vibrations to set the milk in the measuring chamber into vibration, a first measuring means, configured to convert the first vibrations having passed through the milk into first measurement signals, a control device which is configured to control the first vibration means and to process the first measurement signals into at least a quantity that is proportional to the sound velocity in the liquid, in particular the sound velocity in the liquid, further comprising a reference device connected to the control device.

It is known to determine one or more properties of milk by means of sound waves. It is also known that the sound velocity in milk depends on the temperature of the milk. EP 1287737, which is hereby incorporated by reference in its entirety, describes, for example, a method and system to determine milk properties in an acoustic manner, wherein the temperature of the milk is either measured or set at a specific value. It could then be said that the thermometer or the heating or cooling device is the reference device.

A disadvantage of such a device is that the reference device does not always guarantee a reliable measurement, or results in an unnecessarily complex device. There is hardly anything disclosed about the thermometer, and a thermometer has in general the disadvantage that the exact temperature in the whole measuring cell is not known sufficiently well. Additionally, a heating or cooling device has the disadvantage that some time is involved in heating or cooling, which may be undesirable.

BRIEF SUMMARY OF THE INVENTION

It is an object of the present invention to provide a milk property measuring device that enables a more reliable measurement of acoustical properties of milk. A secondary object of the present invention is to provide a device of the aforementioned type, which allows in a simple manner to measure simultaneously a plurality of acoustic properties.

The present invention achieves at least one of the above-mentioned objects by means of a milk property measuring device comprising a measuring chamber configured to house milk; a first vibrator provided at a first side of the measuring chamber, configured to generate first vibrations to set the milk in the measuring chamber into vibration; a first measuring device configured to convert the first vibrations having passed through the milk into first measurement signals; a control device configured to control the first vibrator and to process the first measurement signals into at least a quantity that is proportional to the sound velocity in the liquid further comprising a reference device connected to the control device, wherein the reference device comprises an elongate element provided in the measuring chamber and to be surrounded by the milk filled into the measuring chamber, and a second vibrator configured to generate second vibrations in the elongate element and a second measuring device to convert second vibrations having passed through the elongate element into second measurement signals, wherein the control device is configured to process the second measurement signals into a quantity that is proportional to the sound velocity in the elongate element.

By thus measuring an acoustic quantity in the elongate element, it is possible to establish in particular a temperature of the elongate element, on the basis of for example earlier carried out calibration measurements or on the basis of basic material knowledge. This temperature is a very good reflection of the temperature of the milk as a result of the fact that the elongate element, due to its shape, extends over a relatively large distance in the milk, and as a result thereof takes a temperature gradient in the milk into account in its own acoustic behaviour. Additionally, due to its elongate, thin shape, the elongate element adopts very quickly the temperature of the milk, so that no, or at least only a small measurement deviation and/or time delay in the measurement occurs.

It is pointed out here that by "elongate" there is meant here that the length-thickness ratio of the element amounts to at least 10:1. The elongate element advantageously extends through a substantial part, i.e. at least half, of the measuring chamber, and more advantageously through the entire measuring chamber. As a result thereof, it will be possible to take the temperature of the milk of substantially that substantial part, the entire measuring chamber, respectively, into account. In particular, the elongate element will have a thickness that amounts to not more than 2 mm, and advantageously not more than 1 mm, in order to enable a quick and more accurate temperature measurement. In this case, the element can be designed so as to be hollow, for an even smaller heat capacity, and consequently a quicker temperature adjustment. Furthermore, it is pointed out here that the determination of the sound velocity is equated with the determination of a quantity such as elapsed time, from which the sound velocity can be determined directly.

The acoustic quantity can be determined from the vibrations, advantageously from a time delay that occurs because of the fact that the vibrations move through the medium. In this case, said medium can be both milk and the material of the elongate element. In particular in the case of vibrations transmitted in a pulsed manner, it will be relatively simple to measure a time delay, and consequently the sound velocity, but also other ways of calculating, known to one of ordinary skill in the art, can be used.

In one embodiment, the elongate element is bar-shaped. Such a bar-shaped element, corresponding to a rigid wire-shaped element that does not permanently deform under its own weight, provides the advantage that it will occupy a favourable position in the measuring chamber in almost all circumstances. Moreover, a mechanical tension within the bar does not play a role, and knowledge in this respect is in principle not necessary.

In another embodiment, the elongate element is wire-shaped, by which is meant here that the element is flexible and has no fixed shape without internal tension. Such an element can, for example, be suspended vertically in the measuring chamber. An advantage of a wire-shaped element is that it is can be obtained in a thin shape in a simple manner, and will therefore almost immediately adopt the milk temperature. Another advantage is that it can be strung in a simple manner, and that, in dependence on the tension, it is adjustable to the dimensions of the measuring cell, for example to obtain standing waves with a suitable wavelength. Therefore, in further embodiments, the elongate element, both in case of a bar-shape and a wire-shape, is strung from the first side to a second side of the measuring chamber, in particular an opposite side thereof.

If the elongate element is provided with a free end in the measuring chamber, the free end will reflect the vibrations. In that case, the vibrations can be measured at the same end as where they are provided. If the elongate element is strung at two ends, the vibrations can be measured at any of the two ends.

In a further embodiment, the control device is configured to determine the temperature of the milk from the quantity that is proportional to the sound velocity in the elongate element. As already indicated above, the sound velocity in the elongate element can be determined by determining such a quantity, such as a period of time elapsed between the emission of a wave (pulse) and the detection of a reflection thereof or by determining a wavelength in the element at a known frequency, or can, of course, be determined directly. This can, for example, take place by carrying out calibration measurements, or by searching in tables. On the basis thereof, the temperature of the element, and consequently of the milk, can subsequently be determined. It is subsequently possible to determine, on the basis thereof, whether other, for example simultaneous, acoustic measurements on the milk can be used, because they can, for example, take place at a desired temperature. This determination can be carried out by an operator or automatically.

In particular, the control device is configured to correct the sound velocity measured in the milk, at least the measured quantity that is proportional thereto, for the measured temperature of the milk. As the milk and the elongate element have substantially the same temperature, this temperature can be determined by means of said elongate element. It is then possible, on the basis thereof, to correct the sound velocity measured for the milk to a reference temperature or the like. For this purpose, it is again possible to use calibration functions, which convert the sound velocity measured in the milk at the established temperature into a sound velocity at a standard temperature. This simplifies the comparison of measurements.

In embodiments, the control device is configured to determine the damping of the first and/or the second vibrations. This damping is an indication of the viscosity of the milk, which can therefore be determined in particular from said damping. Such a damping can, for example, be determined by means of wave pattern processing, in particular with continuous waves, such as standing waves, but also with pulses.

In embodiments, the first and second vibrations comprise sound or ultrasound with a frequency between 10 Hz and 200 MHz, in particular ultrasound between 100 kHz and 10 MHz. In practice, such frequencies are found to provide favourable and useful results.

In particular, the first and/or the second vibration means are adjustable with respect to vibration frequency, vibration pattern and/or amplitude. This makes it possible to adjust one or more of these quantities in order thus to achieve optimal measuring results. For example, the vibration frequency can be adjusted in order to obtain a fine standing wave, or the amplitude can be adjusted in order to obtain a good signal-noise ratio with the measuring means.

In embodiments, the first and/or the second vibrators (vibration means) and the first and/or the second measuring devices (measuring means) comprise a piezo element. Piezo elements are very suitable both for generating and for measuring vibrations because of direct coupling with electric voltage. Of course, other vibrators and/or measuring devices are possible as well, for example if large deflections are desired.

In particular, the first and the second vibrators form an integral whole. In this case, it is simple to apply the same vibration both to the milk and to the elongate element, which can simplify the processing of the measuring results. For example in the case of a piezo element, the elongate element can then be attached to the piezo element, which piezo element covers for example a substantial part of a side wall, in particular an end, of the measuring chamber in order thus to make the milk vibrate in a controlled manner.

In advantageous embodiments, the first vibrator and the first measuring device, and/or the second vibrator and the second measuring device are disposed in each case at one side of the measuring chamber. Here, the measuring device will thus measure reflected waves. This offers, for example, an advantage when measuring sound velocity by time elapsed between emitting and measuring a sound wave or pulse, because the trajectory to be covered is in principle twice as long, and consequently the time is twice as long. Here, the elongate element can string (almost) the whole measuring chamber, if desired, although this is not necessary. If not the whole measuring chamber is strung, it will be obvious that a rigid elongate element is advantageous in comparison with a flexible elongate element.

In other embodiments, the first measuring device and/or the second measuring device are provided at a side of the measuring chamber that is different from the side where the first vibrator, the second vibrator, respectively, are provided, in each case in particular at a respective opposite side of the measuring chamber. This provides the possibility to string, for example, a wire as the elongate element through the measuring chamber, which is a very simple and reliable configuration.

For example, the first and the second measuring devices form an integral whole, which offers the advantage of a simple construction. However, it can also be advantageous to provide the first and the second measuring devices as separate elements, for example because the first measuring device measures the vibrations having passed through the milk, which vibrations are longitudinal, and the second measuring device measures the vibrations having passed through the elongate element, which vibrations will for the larger part be transversal. Moreover, the vibrations that pass through the elongate element will usually move at a higher speed than the vibrations that pass through the milk, so that in embodiments in which the measuring device are provided in each case at the opposite side of the vibrator, and an elapsed period of time is measured, the second measuring device will issue a signal at an earlier point of time than the first measuring device.

Advantageously, the measuring chamber has a wall that comprises an acoustically soft material. This means that vibrations incident on the wall will be damped to a high degree, i.e. at least twice as strongly as in the case of steel. In particular, the wall consists of the soft material or is covered on the inside with the soft material. For, it may be advantageous to design the measuring chamber per se of a strong, and therefore often acoustically less damping, material such as steel, while the inner wall is covered with the damping material. More in particular, the material comprises a silicone material, which is a favourable choice in the case of milk, with a view to hygiene requirements.

In embodiments, the elongate element comprises a metal, such as, for example, an alloy. In this case, it is possible to select a strong material which has, by contrast, little damping and which is compatible with milk. Moreover, the element will adopt quickly and completely the temperature of the milk, which results in an enhanced reliability of the measurement.

Other materials, such as ceramic materials, are possible as well. In other embodiments, the elongate element consists of metal-free material, in particular of a plastics material. This offers in particular advantages if, electric measurements are additionally carried out, which could be disturbed by an electrically conductive elongate element. Therefore, the milk property measuring device further comprises an additional device that measures an electric property of the liquid, in particular with the aid of a generated voltage and/or current, more in particular an impedance. Here, by impedance is also meant electric conductivity. This can, for example, be measured by measuring the voltage between two electrodes on both sides of the measuring chamber. The impedance/conductivity is, for example, a good indicator with respect to the health condition (mastitis) of the udder. If desired, also other quantities can be determined, it being pointed out that measuring a plurality of quantities allows the determination of correlations, so that more information can be obtained than merely the sum of the separate parts of information.

In advantageous embodiments, the milk property measuring device further comprises a tightening device for bringing or keeping the elongate element under mechanical tension, in particular under an adjustable mechanical tension. Instead of changing the frequency, it is also possible to change the tension in the elongate element, in order to obtain for example standing waves, or to obtain in another manner a desired wave pattern (wavelength) in the element. In particular, the tightening device comprises a suspension of an elastic material at at least one end of the elongate element. By properly selecting dimensions and elasticity of this suspension, it is possible to ensure a more or less constant tension in the elongate element. Alternatively or additionally, it is possible to provide, for example with an adjusting screw, pneumatically or in any other known manner, an adjustable tension to the element. This is possible by means of a separate suspension of the element, or for example by means of a device to lengthen or shorten the measuring chamber, etc.

The milk property measuring device is advantageously incorporated in a milking device, such as a milking robot. In this case, the milk property measuring device can be configured to examine one or more milk samples per milking. For this purpose, the measuring chamber is then connected by means of a preferably controllable valve system to a milk line of the milking device. In other embodiments, the milk property measuring device is configured for (substantially) continuous measuring, and the measuring chamber is, for example, arranged as a flow measuring chamber. The milking device preferably comprises a control device that controls the milking device on the basis of an outgoing signal from the milk property measuring device, for example a decision to separate milk.

BRIEF DESCRIPTION OF THE DRAWINGS

The features and advantages of the invention will be appreciated upon reference to the following drawings, in which.

DESCRIPTION OF ILLUSTRATIVE EMBODIMENTS

Figure 1:
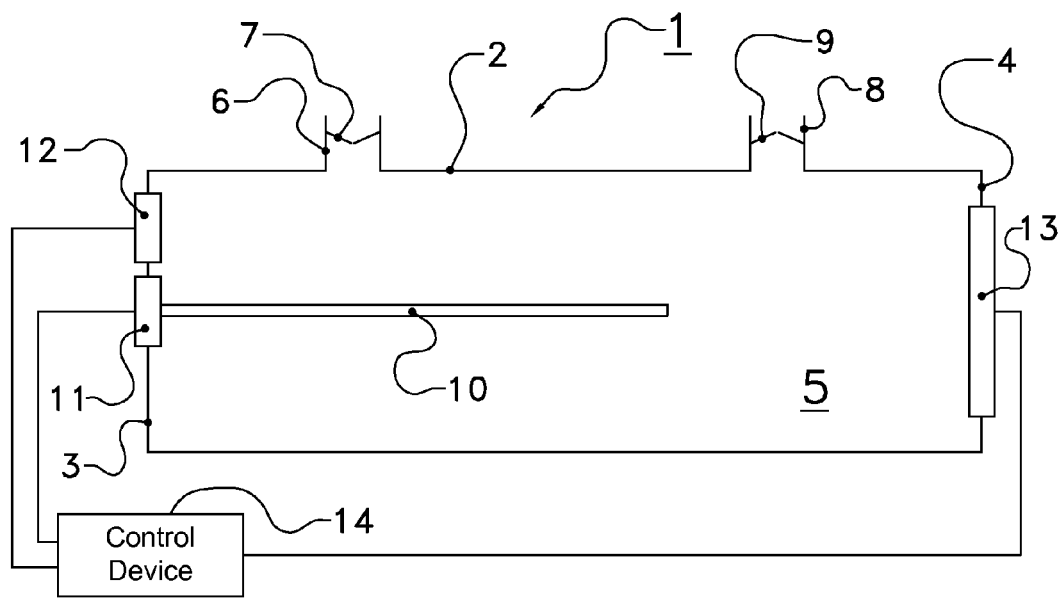
FIG. 1 is a diagrammatic cross-section of a milk property measuring device according to the present invention.

The following is a description of certain embodiments of the invention, given by way of example only and with reference to the drawings. FIG. 1 shows a diagrammatic cross-section of a milk property measuring device according to the invention. In this figure, a measuring chamber is denoted by 1, comprising a wall 2 having a first wall portion 3 and a second wall portion 4. The measuring chamber 1 is filled with milk 5, via a supply 6 with supply valve 7, which milk can be discharged via discharge 8 and discharge valve 9.

Reference number 10 denotes an elongate element, here a metal bar, which is connected to a piezo element 11. Reference number 12 denotes a first measuring means and reference number 13 denotes a first vibration means. Finally, reference number 14 denotes a control device.

The measuring chamber 1 is a somewhat elongate, here cylindrical chamber, which can, for example, also have a square cross-section. In the cylindrical embodiment, the first wall portion 3, the second wall portion 4, respectively, are, for example, each a front surface of the measuring chamber 1.

The measuring chamber 1 can be filled with milk 5 via the supply 6 which is, for example, connected to a milking device, which is illustrated later. The chamber can be emptied via discharge 8 which, for example, debouches into a milk collecting vessel or a waste collecting vessel. The supply 6 and the discharge 8 can be closed by means of a supply valve 7 and a discharge valve 9, respectively, so that, for example, a sample can be taken for testing purposes.

The milk 5 can be tested for acoustic properties, wherein a calibration can take place by means of a bar 10, which can be set into vibration by means of a first piezo element 11, which vibrations can be measured by means of the same first piezo element 11. Likewise, by means of a first measuring means 12 it is possible to measure acoustic vibrations that are transmitted to the milk 5 by means of the first vibration means 13. All this takes place under the control of the control device 14.

In practice, the device operates for example as follows. The vibrations that are generated by the first vibration means 13 will be transmitted as longitudinal waves through the milk 5, and arrive at the measuring means 12. Both in the case of the vibration means 13 and the measuring means 12 piezo elements may be used, but, if desired, electromagnetic coils ("loudspeakers" or microphones) or the like may be used as well. The sound velocity in the milk 5 can, for example, be calculated from the time delay between emission and measurement of the vibrations. Alternatively, the sound velocity can, for example, be determined by means of a standing wave pattern, generated by varying the frequency of the vibrations with the aid of the control device 14. The sound velocity can then also be determined in a simple manner from the determined wavelength and the frequency, which sound velocity is an indication of specific properties of milk, such as the composition thereof. In particular the sound velocity as a function of frequency provides information about fat content, protein content, etc.

The sound velocity strongly depends on the temperature. As, moreover, the milk composition can change, a reference is desired. In order to have a (temperature) reference, there is provided an elongate element in the form of a metal bar 10. This bar can be set into vibration by piezo element 11, which can also measure the vibrations, although a separate measuring element may be provided. This bar has, of course, a fixed composition, and the sound velocity does not depend on the milk composition, but does depend on the milk temperature, which will quickly be adopted by the bar because of its small dimensions. It is simple to calibrate the sound velocity in the bar as a function of the temperature, for example by carrying out a series of measurements under controlled circumstances or by making use of a material having a known sound velocity. This makes it possible to derive the temperature of the milk from the sound velocity measured in the bar 10, so that the sound velocity in milk can be corrected for temperature, and more information about the milk composition can thus be provided. Incidentally, the bar 10 can also be made of other materials, such as plastics, glass, ceramics, etc., as long as it is compatible with milk, and preferably has little own damping.

In addition to the sound velocity, also the damping of vibrations in the bar 10, and, if desired, of the vibrations in the milk 5, can be determined. One can look, for example, at the rate of decrease of the amplitude of the vibrations in the bar 10, corrected for its own damping. Subsequently, on the basis of the damping in the milk 5, extra information about milk composition and the like can be provided in a manner known per se.

Figure 2:
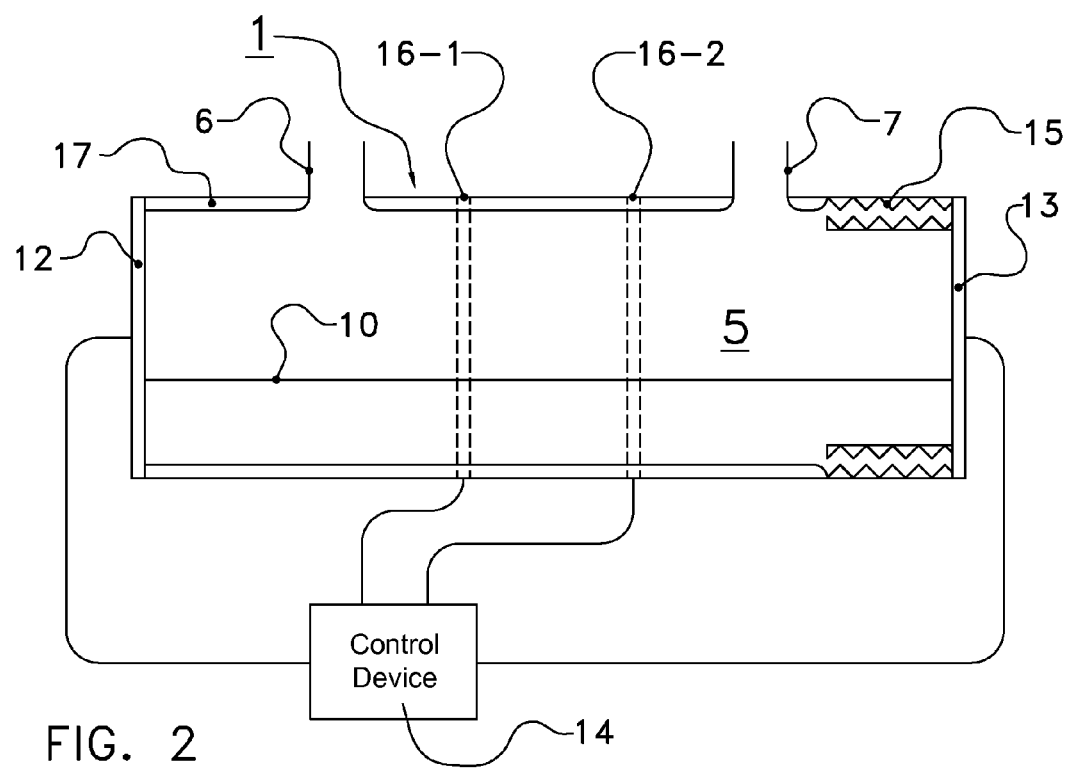
FIG. 2 shows a diagrammatic cross-section of another milk property measuring device according to the invention.

FIG. 2 shows a diagrammatic cross-section of another milk property measuring device according to the invention. Similar components are denoted here, like in the rest of the drawing, by the same reference numerals.

In addition thereto, reference number 15 denotes a tightening device, reference numbers 16-1 and 16-2 denote two ring electrodes and reference number 17 denotes a wall covering.

In the embodiment shown here, the bar is replaced by a wire 10, which is strung between the two front surfaces of the measuring chamber 1, which are again formed themselves by the first measuring means 12, the first vibration means 13, respectively, each constituted also here by a piezo element. A desired mechanical tension can be provided in the wire 10 with the aid of the tightening device 15, which, for example, here comprises a screw thread. By turning in and out the screw, which is connected to the front surface that comprises the vibration means 13, the wire 10 can be strung to a lesser or greater extent. This is, for example, advantageous to generate a suitable wave pattern, with a standing wave, in the wire 10, or to reduce its own damping.

Here, the vibration and measuring means are the same for the wire 10 and for the milk 5. In this case, it can be advantageous to design the vibration pattern of the vibration means 13 complexly, in order thus to be able to generate both longitudinal vibrations, for the milk 5, and transversal vibrations, for the wire 10. Of course, it remains possible to apply separate vibration and/or measuring means.

As the sound velocity in solid substances, such as the wire 10, is usually higher than that in the milk 5, if a sole vibration means 13 is applied, the vibrations through the wire 10 will arrive earlier at the measuring means 12 than the vibrations through the milk 5. As a result of the time difference in arrival between the two paths, it is also possible to determine, at a calculated or known sound velocity in the wire 10, a sound velocity in milk 5.

In order to reduce reflections on the wall of the measuring chamber 1 from the vibrations through the milk, which will ensure a more useful vibration pattern in the milk, the inner wall is covered with acoustically damping wall covering 17, such as silicone material. This material has a much better damping than, for example, steel or other metals or the like, of which the outer part of the measuring chamber will often be made for reasons of strength.

The wire 10, here shown as being eccentrical, which is an alternative arrangement with respect to a centred arrangement, is made in this example of plastics such as synthetic fibre, although, for example, steel or another metal is in many cases a very useful alternative. In this example, however, a metal wire could disturb the operation of the ring electrodes 16-1 and 16-2, which are provided to determine the electric conductivity of the milk 5.

Figure 3:
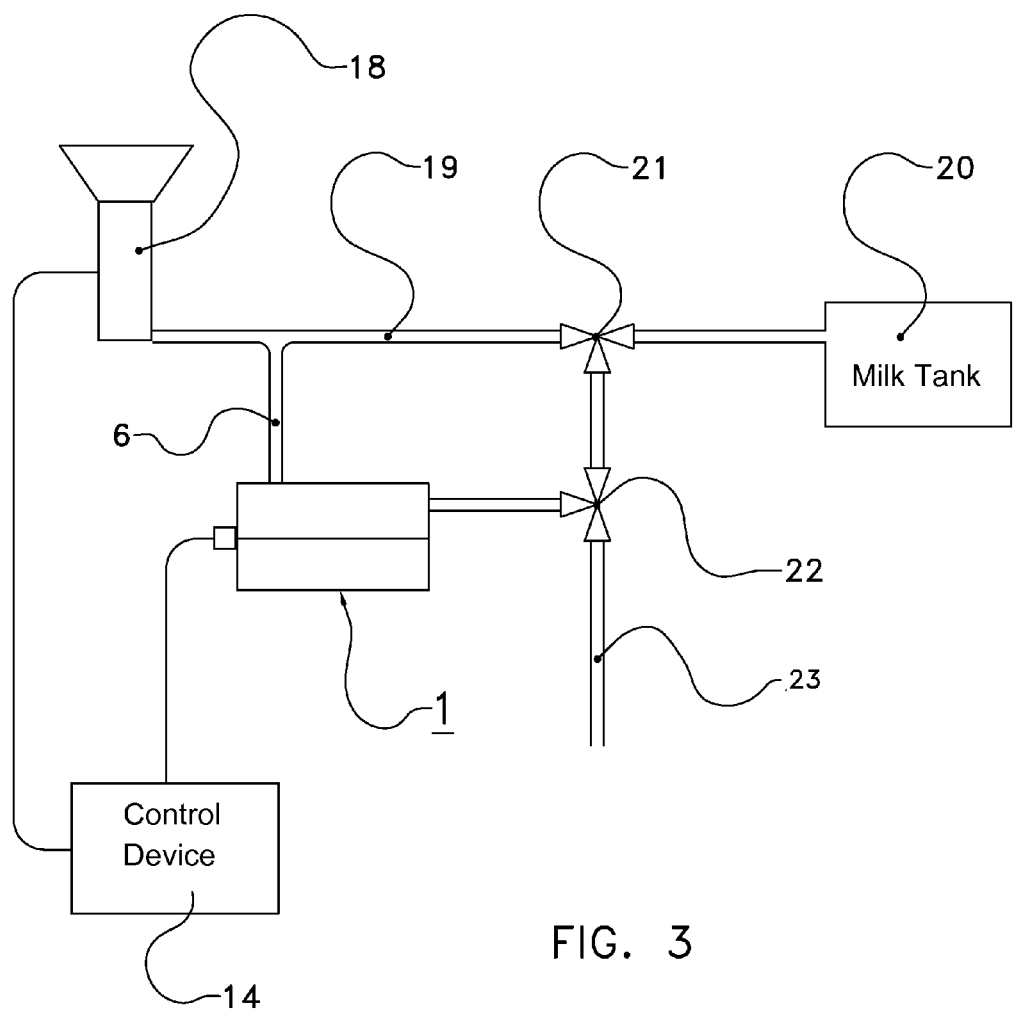
FIG. 3 shows a diagrammatic view of a milking device with a milk property measuring device according to the invention.

FIG. 3 shows a diagrammatic view of a milking device with a milk property measuring device according to the invention.

Reference number 18 is denoted a teat cup which is connected, by means of a milk line 19, to a milk tank 20, and by means of a first multistage valve 21, a second multistage valve 22, respectively, to a separation milk discharge 23.

By means of the teat cup 18 milk can be obtained, a sample of which can be led to the measuring chamber 1 by means of the supply 6. There, the control device 14 can determine a set of properties of the milk, on the basis of which the control device can decide to lead the milk, for example, back to the milk line for storage in the milk tank 20, or to discharge same to the separation milk discharge 23. Something like that can, for example, also hold for the other obtained milk which, by operating the multistage valves 21 and 22 accordingly, can also be led either to the milk tank 20 or to the separation milk discharge 23. In addition to the acoustic measurements in the measuring chamber 1, other measurements can, of course, be carried out as well, on the basis of the total of which the final decision to approve or disapprove the milk can be taken by the control device 14.

Thus, the invention has been described by reference to certain embodiments discussed above. It will be recognized that these embodiments are susceptible to various modifications and alternative forms well known to those of skill in the art. Further modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A milk property measuring device, comprising:
   a measuring chamber configured to house milk;
   a first vibrator provided at a first side of the measuring chamber, configured to generate first vibrations to set the milk in the measuring chamber into vibration;
   a first measuring device configured to convert the first vibrations having passed through the milk into first measurement signals;
   a control device configured to control the first vibrator and to process the first measurement signals into at least a quantity that is proportional to a sound velocity in the milk further comprising a reference device connected to the control device,
   wherein the reference device comprises an elongate element provided in the measuring chamber and to be surrounded by the milk filled into the measuring chamber, and a second vibrator configured to generate second vibrations in the elongate element and a second measuring device to convert second vibrations having passed through the elongate element into second measurement signals, wherein the control device is configured to process the second measurement signals into a quantity that is proportional to the sound velocity in the elongate element,
   wherein the elongate element is a wire-shaped element and is strung from the first side to a second side of the measuring chamber, wherein the control device is configured to determine a temperature of the milk from the quantity that is proportional to the sound velocity in the elongate element, wherein the control device is configured to convert the quantity that is proportional to the sound velocity in the milk at said determined temperature into a quantity that is proportional to a sound velocity in the milk at a standard temperature, and wherein the control device is configured to determine the milk property from said quantity that is proportional to the sound velocity in the milk.

2. The device according to claim 1, wherein the control device is configured to process at least one of the first measurement signals into the sound velocity of the milk and the second measurement signals into the sound velocity of the elongate element.

3. The device according to claim 1, wherein the first side and second side are on opposite sides of the measuring chamber.

4. The device according to claim 1, wherein the control device is configured to determine the damping of the first and/or the second vibrations.

5. The device according to claim 4, wherein the control device is configured to determine the viscosity of the milk from the first and/or the second vibrations.

6. The device according to claim 1, wherein the first and second vibrations comprise sound or ultrasound with a frequency between 10 Hz and 200 MHz.

7. The device according to claim 1, wherein at least one of the first and the second vibrators are adjustable with respect to at least one of a vibration frequency, a vibration pattern and an amplitude.

8. The device according to claim 1, wherein the first and/or the second vibrators and the first and/or the second measuring devices comprise a piezo element.

9. The device according to claim 1, wherein at least one of the first vibrator and the first measuring device, and the second vibrator and the second measuring device are disposed at one side of the measuring chamber.

10. The device according to claim 1, wherein at least one of the first measuring device and the second measuring device are provided at a side of the measuring chamber that is different from the side where the first vibrator, the second vibrator, respectively, are provided at a respective opposite side of the measuring chamber.

11. The device according to claim 1, wherein the first and the second measuring devices form an integral whole.

12. The device according to claim 1, wherein the measuring chamber has a wall that comprises an acoustically soft material.

13. The device according to claim 12, wherein the material comprises a silicone material.

14. The device according to claim 1, wherein the elongate element comprises a metal.

15. The device according to claim 14, further comprising an additional device that measures an electric property of the liquid.

16. The device according to claim 15, wherein the additional device measure the electric property with the aid of at least one of a generated voltage, a current and an impedance.

17. The device according to claim 1, wherein the elongate element consists of at least one of a metal-free material and a plastics material.

18. The device according to claim 1, further comprising a tightening device for bringing or keeping the elongate element under mechanical tension.

19. The device according to claim 18, wherein the tightening device brings or keeps the elongate element under an adjustable mechanical tension.

20. The device according to claim 19, wherein the tightening device comprises a suspension of an elastic material at at least one end of the elongate element.

* * * * *